US010135076B1

(12) United States Patent
 Liu

(10) Patent No.: US 10,135,076 B1
(45) Date of Patent: Nov. 20, 2018

(54) TEAR-ACTIVATED MICRO-BATTERY FOR USE ON SMART CONTACT LENSES

(71) Applicant: Verily Life Sciences LLC

(72) Inventor: Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 73 days.

(21) Appl. No.: 15/138,268

(22) Filed: Apr. 26, 2016

Related U.S. Application Data

(60) Provisional application No. 62/157,123, filed on May 5, 2015.

(51) Int. Cl.
| | |
|---|---|
| H01M 10/44 | (2006.01) |
| H01M 14/00 | (2006.01) |
| H01M 6/32 | (2006.01) |
| H01M 6/40 | (2006.01) |
| G02C 7/04 | (2006.01) |
| A61B 5/00 | (2006.01) |

(Continued)

(52) U.S. Cl.
CPC ............ *H01M 6/32* (2013.01); *A61B 5/0022* (2013.01); *A61B 5/1468* (2013.01); *A61B 5/14507* (2013.01); *A61B 5/14532* (2013.01); *A61B 5/14546* (2013.01); *A61B 5/6821* (2013.01); *G02C 7/04* (2013.01); *H01M 6/40* (2013.01); *H01M 2220/30* (2013.01)

(58) Field of Classification Search
None
See application file for complete search history.

(56) References Cited

U.S. PATENT DOCUMENTS

| | | | |
|---|---|---|---|
| 5,682,210 | A | 10/1997 | Weirich |
| 7,432,069 | B2 | 10/2008 | Barman |
| 8,420,252 | B2 | 4/2013 | Shakespeare et al. |

(Continued)

FOREIGN PATENT DOCUMENTS

JP 4686134 5/2011

OTHER PUBLICATIONS

International Searching Authority, International Search Report and Written Opinion for PCT/US2015/011004, dated Apr. 24, 2015, 13 pages.

*Primary Examiner* — Olatunji A Godo
*Assistant Examiner* — Julian Anthony
(74) *Attorney, Agent, or Firm* — McDonnell Boehnen Hulbert & Berghoff LLP

(57) ABSTRACT

A body-mountable device includes an electrochemical battery configured to provide power when exposed to an aqueous fluid. The aqueous fluid could be blood, sweat, tears, or some other bodily fluid. The electrochemical battery includes an anode that includes zinc metal and is configured to provide an electrical potential relative to a cathode when the anode and cathode are exposed to oxygen and an aqueous fluid. The electrochemical battery could provide power to electronics configured to measure a physiological parameter at a plurality of points in time, to record such measured parameters, to transmit such measured parameters to an external system, or to perform some other functions. Components of the body-mountable device could be embedded in a polymeric material configured for mounting to a surface of an eye. Components of the body-mountable device could be disposed on a flexible substrate configured for mounting to a skin surface.

16 Claims, 9 Drawing Sheets

(51) Int. Cl.
*A61B 5/1468* (2006.01)
*A61B 5/145* (2006.01)

(56) References Cited

U.S. PATENT DOCUMENTS

| | | |
|---|---|---|
| 8,551,308 B2 | 10/2013 | Bhullar |
| 8,755,117 B2 * | 6/2014 | Kobayashi ............ A61F 2/1602 |
| | | 359/558 |
| 2002/0110733 A1 | 8/2002 | Johnson |
| 2008/0139963 A1 | 6/2008 | Carney |
| 2009/0297938 A1 | 12/2009 | Hoofman et al. |
| 2010/0001926 A1 | 1/2010 | Amirparviz et al. |
| 2011/0028807 A1 | 2/2011 | Abreu |
| 2011/0183183 A1 | 7/2011 | Grady et al. |
| 2012/0276434 A1 | 11/2012 | Gaikwad et al. |
| 2012/0283538 A1 | 11/2012 | Rose |
| 2013/0034760 A1 | 2/2013 | Otts et al. |
| 2013/0278887 A1 | 10/2013 | Legerton |
| 2015/0188197 A1 * | 7/2015 | Liu ..................... H01M 4/46 |
| | | 429/163 |
| 2016/0056416 A1 * | 2/2016 | Flitsch ................ H01M 4/134 |
| | | 429/185 |
| 2016/0276678 A1 * | 9/2016 | Jorgensen ............. H01M 6/32 |

* cited by examiner

TEAR-ACTIVATED MICRO-BATTERY FOR USE ON SMART CONTACT LENSES

CROSS-REFERENCE TO RELATED APPLICATION

This application claims priority to U.S. Provisional Patent Application No. 62/157,123, filed May 5, 2015, which is incorporated herein by reference.

BACKGROUND

Unless otherwise indicated herein, the materials described in this section are not prior art to the claims in this application and are not admitted to be prior art by inclusion in this section.

A variety of physiological parameters of a human body can be detected and used to determine a health state or other information about the body (e.g., to determine a blood sugar level, to determine a blood pressure, to determine that the body is in danger from an adverse health state) and/or to perform some activities relating to the body (e.g., to inform a drug dosage, to decide a course of medical treatment, to adjust an athletic training regimen). Such physiological parameters can be detecting at a plurality of points in time and/or across an extended period of time by body-mountable devices that include sensors and other electronic components configured to measure one or more physiological parameters and/or to perform some other functions, e.g., to log and/or record measured physiological parameters, to indicate (e.g., transmit) measured physiological parameters to an external system, or to perform some other function. Such body-mountable devices can be powered by on-board batteries, by energy transmitted from an external system (e.g., transmitted RF energy), by environmental power sources (e.g., motion of the body-mountable device, flexion of the body-mountable device), or some other power source.

SUMMARY

Some embodiments of the present disclosure provide a body-mountable device including: (i) a shaped polymeric material; (ii) a substrate at least partially embedded within the shaped polymeric material; (iii) an electrochemical battery disposed on the substrate and including: (a) a cathode; and (b) an anode that includes zinc metal, wherein the electrochemical battery provides an electrochemical potential between the anode and the cathode when the body-mountable device is exposed to an aqueous fluid; and (iv) one or more electronic components electrically connected to the cathode and the anode, wherein the one or more electronic components are configured to receive power from the electrochemical battery when the body-mountable device is exposed to the aqueous fluid.

Some embodiments of the present disclosure provide a method that includes operating a body-mountable device at a body location where a bodily fluid is at least intermittently present, wherein the body-mountable device includes: (i) a shaped polymeric material; (ii) a substrate at least partially embedded within the shaped polymeric material; (iii) an electrochemical battery disposed on the substrate and including: (1) a cathode; and (2) an anode that includes zinc metal, wherein the electrochemical battery provides an electrochemical potential between the anode and the cathode when the body-mountable device is exposed to the bodily fluid; and (iv) one or more electronic components electrically connected to the cathode and the anode, wherein the operating includes exposing the electrochemical battery to the bodily fluid such that the electrochemical battery provides an electrochemical potential between the anode and the cathode to power the one or more electronic components.

Some embodiments of the present disclosure provide a method including: (i) forming an electrochemical battery on a substrate, wherein the electrochemical battery includes a cathode and an anode, wherein the anode includes zinc metal, wherein forming the electrochemical battery includes forming a layer of zinc metal on a layer of a different metal disposed on the substrate, wherein the electrochemical battery provides an electrochemical potential between the anode and the cathode when the body-mountable device is exposed to an aqueous fluid; (ii) electrically connecting one or more electronic components to the cathode and anode of the electrochemical battery, wherein the one or more electronic components are configured to receive power from the electrochemical battery when the body-mountable device is exposed to the aqueous fluid; and (iii) at least partially embedding the substrate in a shaped polymeric material.

These as well as other aspects, advantages, and alternatives, will become apparent to those of ordinary skill in the art by reading the following detailed description, with reference where appropriate to the accompanying drawings.

DETAILED DESCRIPTION

Figure 1A:
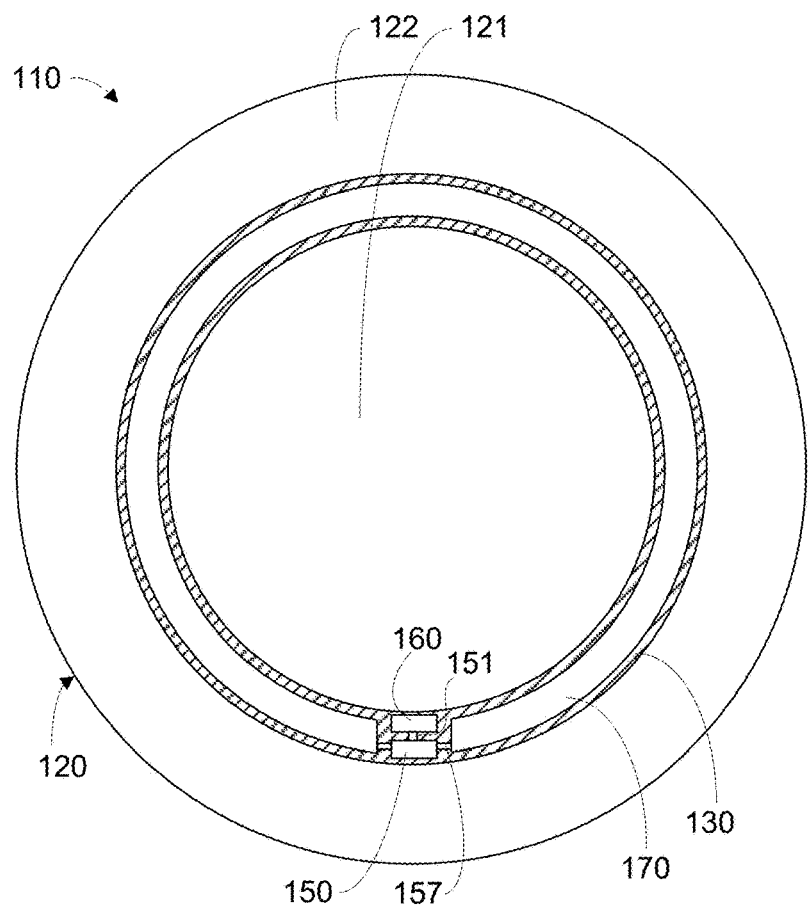
FIG. 1A is a top view of an example eye-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Embodiments provided herein include an electrochemical battery configured to provide an electrochemical potential (e.g., to provide power to electronics connected to the electrochemical battery) when an anode and a cathode of the electrochemical battery are exposed to an aqueous fluid, such as a bodily fluid. The electrochemical battery includes an anode composed of zinc metal, and the aqueous fluid to which the battery is exposed provides an ionic conductive path between the anode and cathode. Oxygen from the environment can diffuse through the aqueous fluid to facilitate oxidization of the zinc metal of the anode. For example, the oxygen could accept electrons from the zinc metal anode via reduction at the cathode when the anode and the cathode are electrically connected, e.g., electrically connected via a load (e.g., one or more electronic components) that is electrically connected to the anode and the cathode. Such electrochemical reactions at the anode and the cathode can generate the provided electrochemical potential between the anode and the cathode. A load connected between the anode and the cathode (e.g., a load including a controller, a sensor, or some other electronic components) could receive power from such an electrochemical battery. Such an electrochemical battery could be stored for an extended period of time, as substantially no current flows between the anode and the cathode of the electrochemical battery when the electrochemical battery is not exposed to an aqueous solution.

Such an electrochemical battery could be provided in a body-mountable device to power electronics or other components of the body-mountable device. In such examples, the aqueous solution to which the electrochemical battery is exposed could be a bodily fluid that is at least intermittently present at the body location where the body-mountable device is mounted, e.g., blood, sweat, tears, interstitial fluid, or some other aqueous bodily fluid. The anode and cathode of the electrochemical battery could be disposed on a substrate (e.g., a flexible printed circuit board) of the body-mountable device. Additional components of the body-mountable device could be disposed on such a substrate, e.g., antennas, electronics, controllers, sensors, or other elements. In some examples, one or more electrochemical sensors (e.g., sensors including respective working electrodes, reference electrodes, counter electrodes, analyte-sensitive substance, and/or other components) could be disposed on such a substrate, e.g., to provide measurement of an analyte (e.g., glucose, an ion, a pH) in the aqueous fluid (e.g., an interstitial fluid, a tear fluid) to which the body-mountable device is exposed. A body-mountable device could be configured to operate sensors (e.g., such electrochemical sensors, optical sensors, temperature sensors) to measure physiological parameters of a body to which the body-mountable device is mounted and to record, transmit, or otherwise operate based on such measurements.

In some embodiments, the body-mountable device is configured to detect a concentration, presence, or other properties of an analyte in fluid to which the body-mountable device is exposed. For example, the body-mountable device could be an eye-mountable device (e.g., could be and/or could be formed as part of an ophthalmic lens configured to be removably mounted to a corneal surface of an eye) and could be configured and/or operated to detect a level of glucose, urea, pyruvate, potassium, phosphate, or other analytes in a tear fluid of the eye. Such measured concentrations could be used to determine a health state (e.g., that a wearer of the body-mountable device is experiencing a hyperglycemic or hypoglycemic event) or other information (e.g., a blood glucose level) of the body to which the device is mounted. Such measurements could be performed using the body-mountable device a plurality of times, and a plurality of respectively detected analyte concentrations or other properties could be recorded to a memory of the device (e.g., to be accessed later by an external system), transmitted to an external system (e.g., using an antenna, using an infrared light emitter), or used to provide some other function (e.g., used to generate an alert that could be indicated to a user of the device by emitted light from a light-emitting diode of the device).

When exposed to an aqueous solution, the zinc metal of the anode of the electrochemical battery can be oxidized to zinc hydroxide. Zinc hydroxide is substantially insoluble in water, such that the zinc hydroxide formed when the electrochemical battery is exposed to an aqueous solution will substantially remain proximate to the electrochemical battery, i.e., will substantially not contaminate an aqueous fluid to which the electrochemical battery is exposed. Further, an electrochemical potential produced between the zinc-metal anode and the cathode could be between approximately 0.8 volts and approximately 0.9 volts, less than a voltage difference sufficient to electrolyze water in the aqueous solution. The anode could be composed completely of zinc metal or could be composed of additional metals or other materials. For example, the anode could include a layer of zinc metal disposed on a layer of a different metal (e.g., a metal trace) that is disposed on a substrate on which the electrochemical battery is disposed. The cathode of the electrochemical cell could be composed of a variety of materials such that oxygen can be reduced at the cathode. In some examples, the cathode includes platinum metal. The cathode could be composed completely of platinum metal or could include a layer of platinum metal disposed on a layer of a different metal (e.g., by sputtering and/or photolithography). The electrochemical battery could include additional elements, e.g., a water-permeable protective layer (e.g., a layer composed of a hydrogel) disposed on the anode and the cathode to protect the electrochemical battery from elements in the environment of the electrochemical battery. The anode and the cathode of the electrochemical battery could be formed in a variety of ways to, e.g., maximize an energy capacity, minimize a size, minimize a material cost, or control some other property of the electrochemical battery. In some examples, the anode and the cathode could include respective pluralities of interdigitated elongate extensions.

Body-mountable devices as described herein could take a variety of forms and be configured in a variety of ways to be mounted on body locations according to an application. Such devices could include mounts (e.g., straps, adhesives) or other features (e.g., a geometry configured to conform to and/or around an element of human anatomy) configured to position the body-mountable device relative to a target portion of a body such that the electrochemical battery can be exposed to an aqueous solution and thus provide power to the body-mountable device, e.g., to provide power to detect a physiological parameter of the portion of the body to which the body-mountable device is mounted.

In some examples, a body-mountable device could additionally be powered by radiated energy received at the body-mountable device. Such received radiated energy could be used to power additional operations of the body-mountable device, e.g., to perform calculations on measurements made by the body-mountable device when powered by the electrochemical battery, to transmit such measurements, or to perform some other operations. Such received radiated energy could be rectified and/or regulated in real time to power the body-mountable device. For example, power can be generated from incident radio frequency radiation inductively harvested by a suitable antenna of the body-mountable device. A rectifier and/or regulator can then output a stable DC voltage to power the body-mountable device. Such an antenna can be arranged as a loop of conductive material that is connected to electronics of the body-mountable device. Furthermore, the body-mountable device can be configured to wirelessly communicate information (e.g., a signal related to a digital output of the sigma-delta modulator) to an external system by modifying the impedance of the antenna so as to characteristically modify RF backscatter from the antenna in a manner that can be detected by the external system.

In some embodiments, the body-mountable device is situated in an eye-mountable device configured to rest on corneal tissue, similar to a contact lens. The electrochemical battery of such an eye-mountable device is configured to receive a tear fluid of the eye such that the electrochemical battery provides an electrochemical potential, e.g., to power the eye-mountable device. The eye-mountable device could include an electrochemical sensor (e.g., two or more electrodes) to detect an analyte in tear fluid of the eye or could include additional or alternative sensors or other components configured to provide other functions of the eye-mountable device. The electrochemical battery (e.g., the anode and cathode thereof) and other elements of such an eye-mountable device (e.g., electronics, sensors, antennas) can be disposed on a substrate embedded in the lens material. The substrate can be embedded near the periphery of the eye-mountable device, such as a ring-shaped substrate embedded in the contact lens material around the circumference, so as to avoid interference with light transmission to the pupil near the central portion of the contact lens. The electrochemical battery and/or electrochemical or other sensor(s) can be arranged on the substrate to face inward, toward the surface of the cornea, to receive an aqueous fluid (i.e., a tear fluid) from a tear film disposed between the cornea and the eye-mountable device. The electrochemical battery and/or electrochemical or other sensor(s) may additionally or alternatively be arranged to face outward, away from the surface of the cornea, to receive an aqueous fluid from a tear film disposed on the outer surface of the eye-mountable device (e.g., a tear film deposited on the outer surface of the eye-mountable device by eyelid motion).

In some examples, an external reader can communicate with a body-mountable device, e.g., can receive information related to one or more measurements made by the body-mountable device, e.g., while powered by the electrochemical battery. In such examples, the external reader could radiate radio frequency radiation to power the body-mountable device via an energy harvesting system. The external reader may thereby control the operation of the body-mountable device by providing power to the body-mountable device that is additional or alternative to power provided by the electrochemical battery. In some examples, the external reader can operate to intermittently interrogate the body-mountable device to provide a reading by radiating sufficient radiation to power the body-mountable device to perform some operations based on one or more measurements performed by the body-mountable device (e.g., to calculate a value of a physiological property based on a measurement made using an electrochemical sensor), to communicate information related to one or more measurements (e.g., to communicate a calculated physiological property), or to perform some other operations (e.g., to operate a sensor of the body-mountable device that requires more power than is provided by the electrochemical battery). The external reader can also store sensor results or other information communicated by the body-mountable device. In this way, the external reader can acquire a plurality of sensor measurements or other information over time without continuously powering the body-mountable device.

The external reader may be provided as a mobile device with software applications for displaying the sensor results. The external reader may also include a communications interface that can be configured to convey measured and/or determined information to other systems for display, data storage, and/or analysis.

II. EXAMPLE ELECTROCHEMICAL BATTERY AND OPHTHALMIC DEVICE

An electrochemical battery as described herein (i.e., an electrochemical battery that includes a zinc-metal anode and a cathode disposed on a substrate and configured to provide an electrochemical potential when exposed to an aqueous solution) could be incorporated into a variety of devices or systems and used to provide power for a variety of different applications of such systems. In some examples, the electrochemical battery could be incorporated into a body-mountable device such that, when the body-mountable device is mounted to a body and exposed to aqueous fluids of the body (e.g., blood, sweat, tears, interstitial fluids, etc.), the electrochemical battery provides power to the body-mountable device. Such a body-mountable device could include sensors (e.g., sensors configured to detect an analyte in the body fluid(s) to which the body-mountable device is exposed), transmitters, antennas, light-emitting elements, controllers, or other components according to an application. Such body-mountable devices could be configured to mount to a skin surface (e.g., to have an electrochemical battery that receives sweat from the skin, to have an electrochemical battery and/or sensors disposed on an elongate probe element configured to penetrate the skin and to expose the battery and/or sensors to interstitial fluid and/or blood), to be mounted to a surface within a mouth or other gastrointestinal tissue(s) and/or to be otherwise disposed within such, to be disposed within a body cavity (e.g., a cranial cavity, a pleural cavity, a peritoneal cavity) and/or within a body tissue, to be mounted to an eye, or to by disposed on within a body in some other way.

Figure 1B:
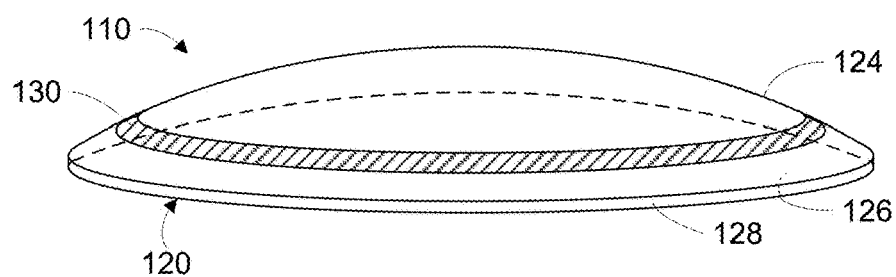
FIG. 1B is an aspect view of the example eye-mountable device shown in FIG. 1A.

FIG. 1A is a top view of an example eye-mountable electronic device 110. FIG. 1B is an aspect view of the example eye-mountable electronic device shown in FIG. 1A. It is noted that relative dimensions in FIGS. 1A and 1B are not necessarily to scale, but have been rendered for purposes of explanation only in describing the arrangement of the example eye-mountable electronic device 110. The eye-mountable device 110 is formed of a polymeric material 120 shaped as a curved disk. The polymeric material 120 can be a substantially transparent material to allow incident light to be transmitted to the eye while the eye-mountable device 110 is mounted to the eye. The polymeric material 120 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 120 can be formed with one side having a concave surface 126 suitable to fit over a corneal surface of an eye. The opposing side of the disk can have a convex surface 124 that does not interfere with eyelid motion while the eye-mountable device 110 is mounted to the eye. A circular outer side edge 128 connects the concave surface 124 and convex surface 126.

The eye-mountable device 110 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 110 can be selected according to the size and/or shape of the corneal surface of the wearer's eye.

The polymeric material 120 can be formed with a curved shape in a variety of ways. For example, techniques similar to those employed to form vision-correction contact lenses, such as heat molding, injection molding, spin casting, etc. can be employed to form the polymeric material 120. While the eye-mountable device 110 is mounted in an eye, the convex surface 124 faces outward to the ambient environment while the concave surface 126 faces inward, toward the corneal surface. The convex surface 124 can therefore be considered an outer, top surface of the eye-mountable device 110 whereas the concave surface 126 can be considered an inner, bottom surface. The "top" view shown in FIG. 1A is facing the convex surface 124. From the top view shown in FIG. 1A, the outer periphery 122, near the outer circumference of the curved disk is curved into the page, whereas the center region 121, near the center of the disk is curved out of the page.

A substrate 130 is embedded in the polymeric material 120. The substrate 130 can be embedded to be situated along the outer periphery 122 of the polymeric material 120, away from the center region 121. The substrate 130 does not interfere with vision because it is too close to the eye to be in focus and is positioned away from the center region 121 where incident light is transmitted to the eye-sensing portions of the eye. Moreover, the substrate 130 can be formed of a transparent material to further mitigate any effects on visual perception.

The substrate 130 can be shaped as a flat, circular ring (e.g., a disk with a central hole). The flat surface of the substrate 130 (e.g., along the radial width) is a platform for mounting electronics such as chips (e.g., via flip-chip mounting) and for patterning conductive materials (e.g., via deposition techniques) to form electrodes (e.g., an anode and/or cathode of an electrochemical battery, electrodes of an electrochemical sensor), antenna(e), and/or connections. The substrate 130 and the polymeric material 120 can be approximately cylindrically symmetric about a common central axis. The substrate 130 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 130 can be implemented in a variety of different form factors.

A loop antenna 170, controller 150, and electrochemical battery 160 are disposed on the embedded substrate 130. The controller 250 can be a chip including logic elements configured to receive power from the electrochemical battery 160 and to operate the loop antenna 170. The controller 150 is electrically connected to the loop antenna 170 by interconnects 157 also situated on the substrate 130. Similarly, the controller 150 is electrically connected to the electrochemical battery 160 by an interconnect 151. The interconnects 151, 157, the loop antenna 170, and any conductive electrodes (e.g., an anode and cathode of the electrochemical battery 160, for an electrochemical ion sensor, etc.) can be formed from conductive materials patterned on the substrate 130 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 1A, which is a view facing the convex surface 124 of the eye-mountable device 110, the electrochemical battery 160 is mounted to a side of the substrate 130 facing the convex surface 124. However, the electronics, electrochemical battery, etc. situated on the substrate 130 can be mounted to either the "inward" facing side (e.g., situated closest to the concave surface 126) or the "outward" facing side (e.g., situated closest to the convex surface 124). Moreover, in some embodiments, some electronic components can be mounted on one side of the substrate 130, while other electronic components are mounted to the opposing side, and connections between the two can be made via conductive materials passing through the substrate 130.

The loop antenna 170 can be a layer of conductive material patterned along the flat surface of the substrate to form a flat conductive ring. In some instances, the loop antenna 170 can be formed without making a complete loop. For instance, the antenna 170 can have a cutout to allow room for the controller 150 and electrochemical battery 160, as illustrated in FIG. 1A. However, the loop antenna 170 can also be arranged as a continuous strip of conductive material that wraps entirely around the flat surface of the substrate 130 one or more times. For example, a strip of conductive material with multiple windings can be patterned on the side of the substrate 130 opposite the controller 150 and bio-interactive electronics 160. Interconnects between the ends of such a wound antenna (e.g., the antenna leads) can be passed through the substrate 130 to the controller 150.

Figure 1D:
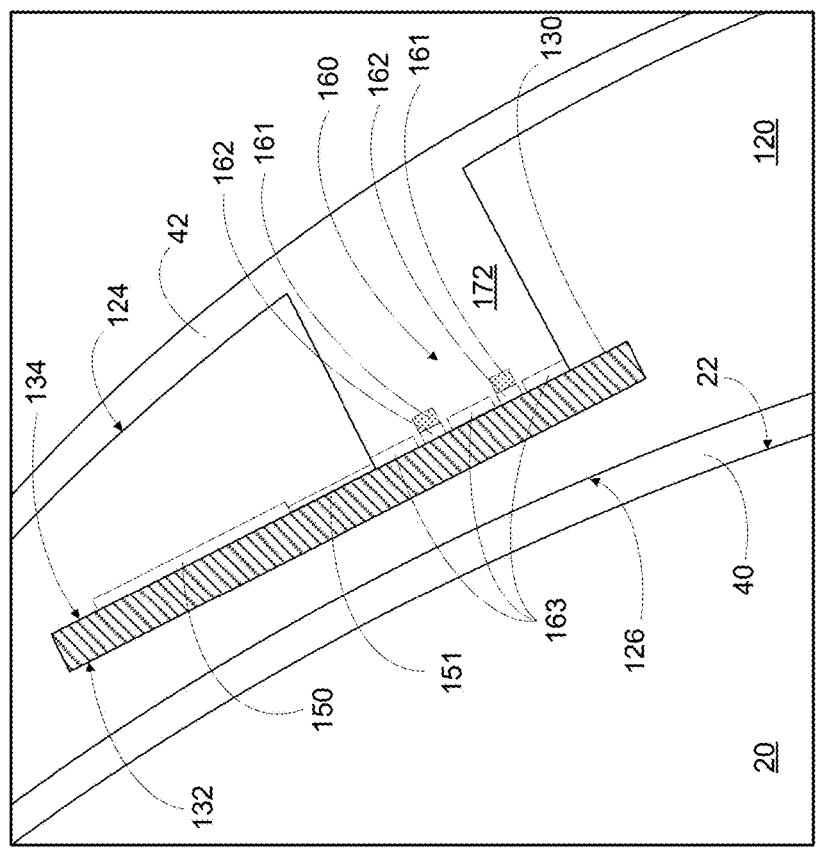
FIG. 1D is a side cross-section view enhanced to show the tear film layers surrounding the surfaces of the example eye-mountable device when mounted as shown in FIG. 1C.
Figure 1C:
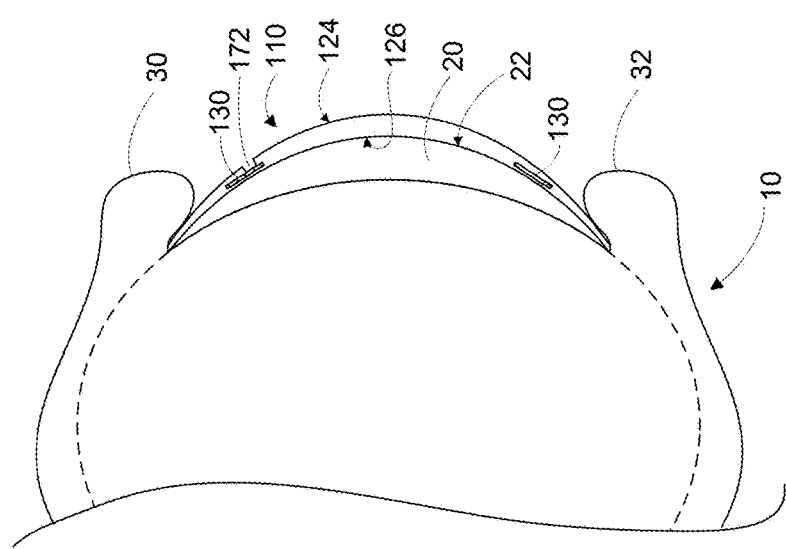
FIG. 1C is a side cross-section view of the example eye-mountable device shown in FIGS. 1A and 1B while mounted to a corneal surface of an eye.

FIG. 1C is a side cross-section view of the example eye-mountable electronic device 110 while mounted to a corneal surface 22 of an eye 10. FIG. 1D is a close-in side cross-section view enhanced to show the tear film layers 40, 42 surrounding the exposed surfaces 124, 126 of the example eye-mountable device 110. It is noted that relative dimensions in FIGS. 1C and 1D are not necessarily to scale, but have been rendered for purposes of explanation only in describing the arrangement of the example eye-mountable electronic device 110. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous fluid secreted by the lacrimal gland to protect and lubricate the eye 10. When the eye-mountable device 110 is mounted in the eye 10, the tear film coats both the concave and convex surfaces 124, 126 with an inner layer 40 (along the concave surface 126) and an outer layer 42 (along the convex layer 124). The tear film layers 40, 42 can be about 10 micrometers in thickness and together account for about 10 microliters.

The tear film layers 40, 42 are distributed across the corneal surface 22 and/or the convex surface 124 by motion of the eyelids 30, 32. For example, the eyelids 30, 32 raise and lower, respectively, to spread a small volume of tear film across the corneal surface 22 and/or the convex surface 124 of the eye-mountable device 110. The tear film layer 40 on the corneal surface 22 also facilitates mounting the eye-mountable device 110 by capillary forces between the concave surface 126 and the corneal surface 22. In some embodiments, the eye-mountable device 110 can also be held over the eye in part by vacuum forces against corneal surface 22 due to the concave curvature of the eye-facing concave surface 126.

As shown in the cross-sectional views in FIGS. 1C and 1D, the substrate 130 can be inclined such that the flat mounting surfaces of the substrate 130 are approximately parallel to the adjacent portion of the concave surface 126. As described above, the substrate 130 is a flattened ring with an inward-facing surface 132 (closer to the concave surface 126 of the polymeric material 120) and an outward-facing surface 134 (closer to the convex surface 124). The substrate 130 can have electronic components and/or patterned conductive materials mounted to either or both mounting surfaces 132, 134. As shown in FIG. 1D, the electrochemical battery 160, controller 150, and conductive interconnects 151 are mounted on the outward-facing surface 134 such that the electrochemical battery 160 is relatively closer in proximity to the outer tear film layer 42 than if it was mounted on the inward-facing surface 232. With this arrangement, the electrochemical battery 160 can receive tear fluid from the outer tear film 42 and oxygen from the atmosphere through a channel 172 formed in the polymeric material 120 and extending from the convex surface 124. However, in other examples, the electrochemical battery 160 may be mounted on the inward-facing surface 132 of the substrate 130 such that the electrochemical battery 160 is facing the convex surface 124 and able to receive aqueous fluid from the inner tear film layer 40.

As shown in cross-section in FIG. 1D, the electrochemical battery 160 includes at least one cathode 163 and at least one anode comprising zinc metal 161 disposed on metal traces 162. When the electrochemical battery 160 is exposed to an aqueous fluid (e.g., to tears from the outer tear layer 42 delivered via the channel 172), an electrochemical potential develops between the anode 161/162 and the cathode 163. The developed electrochemical potential is related to electrochemical reactions occurring between water and oxygen in the fluid and the cathode 163 and the zinc metal 161 of the anode. At the zinc metal 161 of the anode, these reactions include oxidation of the zinc metal by chemicals in the fluid to form zinc hydroxide on the surface of the zinc metal 161. This reaction can be represented by:

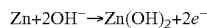

wherein the electrons can contribute to a current out of the anode 161/162 (i.e., a flow of electrons into the anode 161/162) that can be used to power electronics of the eye-mountable device 110. The zinc hydroxide formed in this reaction is substantially insoluble in water and so will substantially remain proximate to the zinc metal 161 of the anode. The cathode 163 can include a number of metals configured to reduce oxygen. This reaction can be represented by:

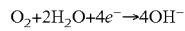

wherein the electrons can contribute to a current into the cathode 163 (i.e., a flow of electrons out of the cathode 163) to balance a corresponding current into the anode 161/162. The cathode 163 could be composed of a variety of metals configured to provide such reactions, e.g., the cathode 163 could include platinum (e.g., could be composed of platinum, could include metal traces coated, plated, or otherwise including a surface layer of platinum) and/or alloys of platinum.

Figure 2A:
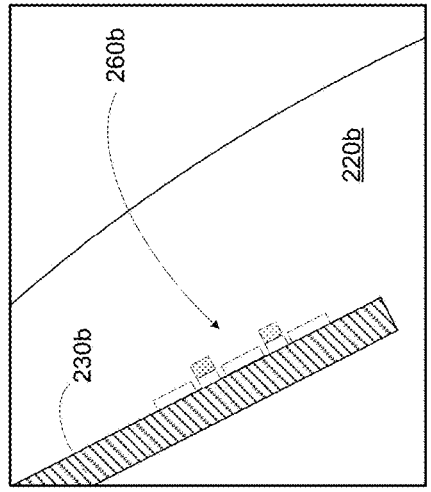
FIG. 2A is a side cross-section view of an electrochemical battery of a body-mountable device.

Note that the anode 161/162 and cathode 163 of the electrochemical battery 160 being exposed directly to the environment of the eye-mountable device 110 (e.g., exposed directly to fluids received from the outer teary layer 42 via the channel 172) is meant as a non-limiting example. For example, an electrochemical battery could include a protective coating that is disposed over the anode 161/162 and the cathode 163 and that is permeable to water and oxygen from an aqueous fluid, e.g., from a bodily fluid to which a body-mountable device including the electrochemical battery is exposed. FIG. 2A shows, in cross-section, an electrochemical battery 260a as described elsewhere herein that is disposed on a substrate 230a that is at least partially embedded in a shaped polymeric material 220a. A channel 272a is formed in the shaped polymeric material 220a between the electrochemical battery 260a and an environment of the electrochemical battery 260a (e.g., an environment that includes an aqueous fluid). A protective layer 290a is disposed in the channel 272a. The protective layer 290a could be a hydrogel or other material that is permeable to water and to oxygen and that has a hardness, a stiffness, a resilience, or some other property specified to protect the elements (e.g., anodes, cathodes) of the electrochemical battery 260a. For example, the protective layer 290a could be a hydrogel that includes units of hydroxyethyl methacrylate. The protective layer 290a could include one or more polymers, including polydimethylsiloxane, polyvinylchloride, polyethylene terephthalate, polymethyl methacrylate, silicone hydrogels, or combinations of these or other polymers. The embodiments herein are meant only as illustrative examples; other protective layers and electrode materials are anticipated.

Figure 2B:
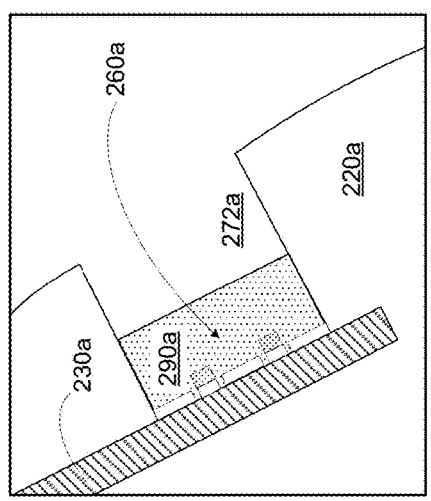
FIG. 2B is a side cross-section view of an electrochemical battery of a body-mountable device.
Figure 2C:
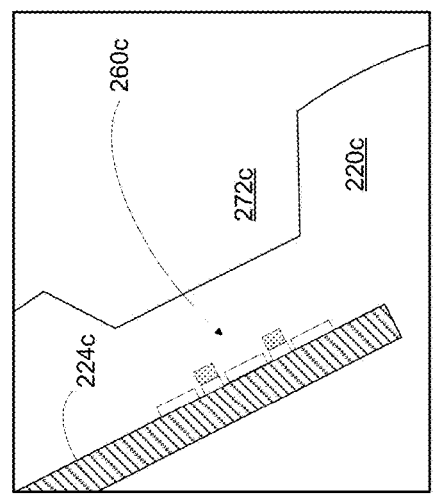
FIG. 2C is a side cross-section view of an electrochemical battery of a body-mountable device.

Additionally or alternatively, a shaped polymer (e.g., an ophthalmic lens or other structure formed to at least partially encapsulate elements of a body-mountable device) of a body-mountable device could be permeable to water and to oxygen and could be formed over and/or as part of an electrochemical battery to protect elements (e.g., an anode and/or cathode) of the electrochemical battery. FIG. 2B shows, in cross-section, an electrochemical battery 260b as described elsewhere herein that is disposed on a substrate 230b that is at least partially embedded in a shaped polymeric material 220b. The shaped polymeric material 220b could be a hydrogel or other material that is permeable to water and to oxygen and that has a hardness, a stiffness, a resilience, thickness, or some other property specified to protect the elements (e.g., anodes, cathodes) of the electrochemical battery 260a. For example, the protective layer 290a could be a hydrogel that includes units of hydroxyethyl methacrylate. In some examples, a thickness of the shaped polymeric material (e.g., 220b) overlaying an electrochemical battery could be specified to provide a sufficient amount of water and/or oxygen to the electrochemical battery (e.g., an amount such that an amount of power provided by the electrochemical battery to electronics is greater than some specified amount). FIG. 2C shows, in cross-section, an electrochemical battery 260c as described elsewhere herein that is disposed on a substrate 230c that is at least partially embedded in a shaped polymeric material 220c. The shaped polymeric material 220c includes a formed depression 272c proximate the electrochemical battery 260c such that a thickness of the shaped polymeric material 220c over the electrochemical battery 260c (e.g., an amount of the shaped polymeric material 220c intervening between the electrochemical battery 260c and an aqueous fluid in an environment of the electrochemical battery 260c) is substantially equal to some specified thickness.

Anodes, cathodes, and other elements of an electrochemical battery as described herein could be configured in a variety of ways according to an application. A geometry, shape, size, thickness, spacing, or other properties of one or more anodes and/or cathodes of an electrochemical battery could be specified to provide a power capacity, an energy capacity, an overall area or volume, a resistance to degradation of the zinc metal while in storage, to reduce an amount of diffusion of electrochemical species (e.g., hydroxide ions) away from the electrochemical battery, or to provide some other feature or function. For example, a total area and/or volume of zinc metal could be specified to provide a specified energy capacity of an electrochemical battery. For example, an anode of an electrochemical battery could include approximately 0.1 square millimeters of approximately 20 micron thick zinc metal (corresponding to approximately 14 micrograms of zinc metal) such that the electrochemical battery provides at least approximately 12 microamp-hours of energy (corresponding to at least approximately 0.82 amp-hours of energy per gram of zinc metal or at least approximately 5.8 amp-hours of energy per cubic centimeter of zinc metal). In some examples, the anode and cathode of an electrochemical battery could include elongate elements or other features that are interdigitated, e.g., to maximize an area of the anode (and of zinc metal thereof) that is within some specified maximum distance from an area of the cathode.

Figure 3A:
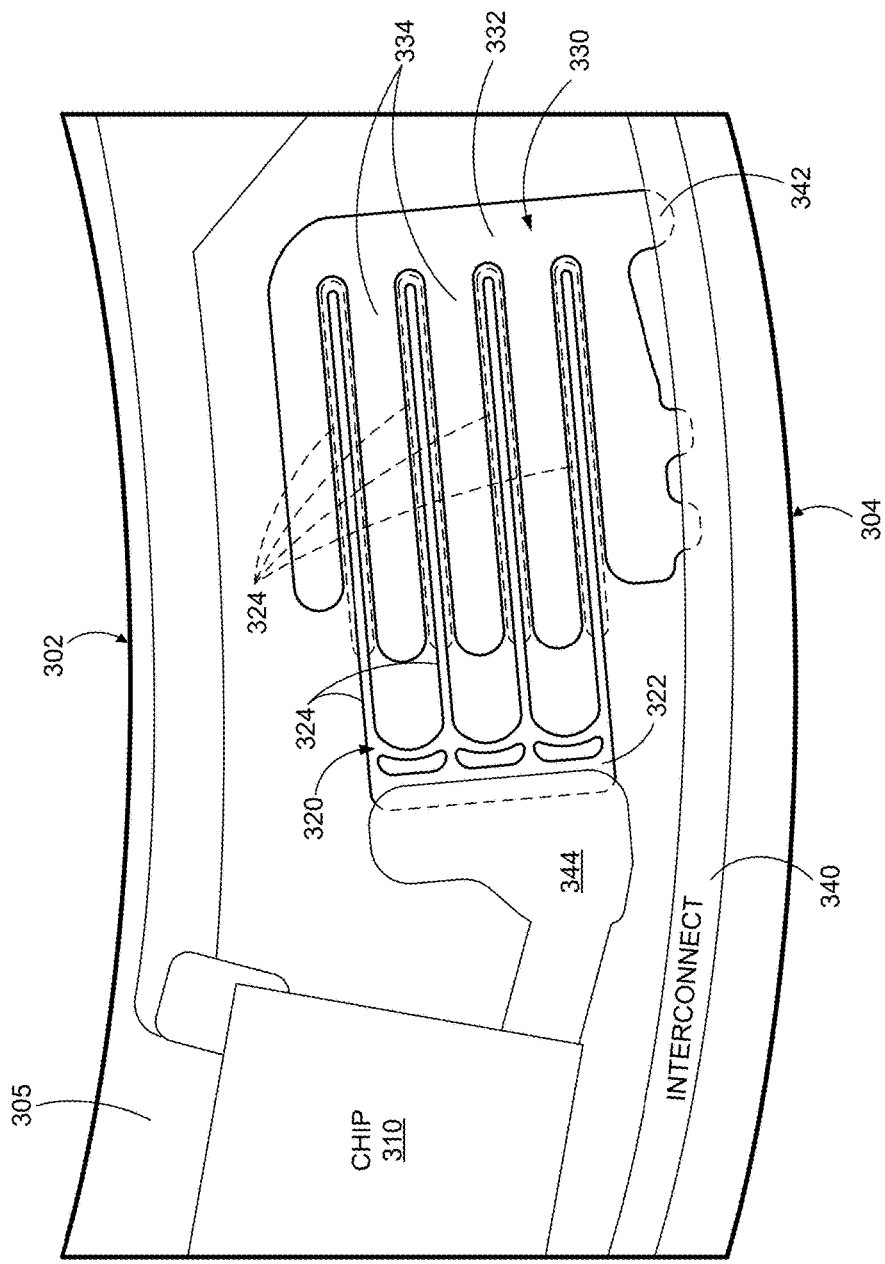
FIG. 3A illustrates an example arrangement for electrodes in an electrochemical battery disposed on a surface of a body-mountable device.

FIG. 3A illustrates an example arrangement for interdigitated electrodes in an electrochemical battery disposed on a surface of a flattened ring substrate. FIG. 3A illustrates a portion of a substrate 305 on which an electrochemical battery is mounted. The substrate 305 is configured to be embedded in an eye-mountable or otherwise body-mountable device and can be similar to the substrate 120 described above in connection with FIGS. 1A-1D. The substrate 305 can be shaped as a flattened ring with an inner edge 302 and an outer edge 304. The two edges 302, 304 may both be at least approximately circular, although only a portion of each is shown in FIG. 3A.

The substrate 305 provides a mounting surface for mounting a chip 310 and for patterning battery anodes, battery cathodes, sensor electrodes, antennas, conductive interconnects, or other elements between pads or terminals on the chip 310 and the other components. An electrochemical battery includes an anode 320 and a cathode 330 patterned on the substrate 305. The anode 320 is electrically connected to a connection pad of the chip 310 through an interconnect 344. The cathode 330 can then be electrically connected to another pad (not visible) on the chip 310 via the interconnect 340 that connects to the cathode 330 at multiple overlap points 342.

The anode 320 includes a layer of zinc metal 324 disposed on a layer of a different metal (e.g., copper, gold, platinum, or some other metal) that is configured with a base section 322 and a number of elongate extensions 324. The layer of zinc metal 324 can be formed by photopatterning, sputtering, electroplating, or other methods. The cathode 330 includes metal (e.g., platinum, platinum disposed on traces of some other metal) formed to have a base section 332 and a number of elongate extensions 324 that are interdigitated with the elongate extensions 324 of the anode 320. A separation between the elongate extensions 324 of the anode 320 and the elongate extensions 334 of the cathode 330 could be specified to, e.g., reduce a mean distance between locations of the zinc metal 324 and locations of the cathode 630, to control an internal resistance of the electrochemical battery, or according to some other consideration. A relationship between the area of the anode and the area of the cathode (or, relatedly, the width of elongate extensions thereof, e.g., 324, 334) could be specified to provide a minimum power capacity of the electrochemical battery or according to some other consideration. For example, the elongate extensions 324 of the anode 320 could have widths of approximately 50 microns and the elongate extensions 334 of the cathode 330 could have widths of approximately 250 microns.

The chip 310 can also be connected to other components via additional connection pads. For example, as shown in FIG. 3A, the chip 310 can be connected to an antenna lead, which can be formed of a patterned conductive material, such as electroplated gold, for example, that substantially circles the substrate 305 to create a loop antenna.

Figure 3B:
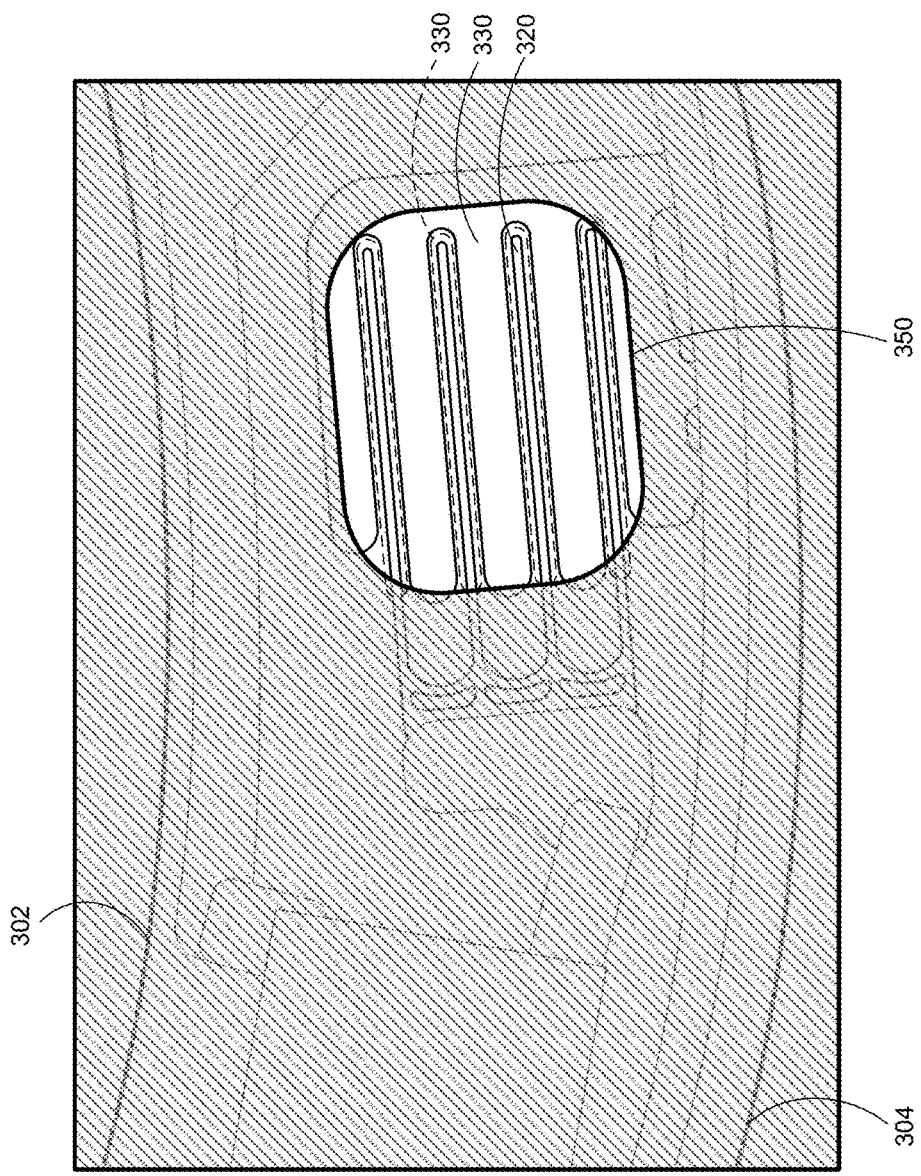
FIG. 3B illustrates the arrangement in FIG. 3A when embedded in a shaped polymeric material with a channel positioned to expose the electrochemical battery electrodes.

FIG. 3B illustrates the arrangement in FIG. 3A when embedded in a polymeric material with a channel 350 positioned to expose the anode 320 and cathode 330 of the electrochemical battery to an aqueous fluid. In FIG. 3B, the polymeric material is illustrated by the hash pattern that is superimposed over the portion of the substrate 305 shown in FIG. 3A. The channel 350 may be formed by removing a portion of the encapsulating polymeric material (e.g., by etching, by removing a layer defined by a photoresist, etc.). Additionally or alternatively, the channel 350 could be formed by molding the polymeric material using a mold that surrounds the substrate 305 and elements disposed thereon and that includes a protraction corresponding to the channel 350. The channel 350 exposes a region including the anode 320 and cathode 330 of the electrochemical battery, such that the electrochemical battery can be exposed to a tear film coating the polymeric material and the electrochemical battery is able to provide an electrochemical potential, e.g., to power circuitry of the chip 310. Alternatively, the channel 350 could represent a thinner region of the polymeric material, could include a protective layer formed on the anode and cathode of the electrochemical battery, or could be configured in some other way. In some examples, the polymeric material could lack the channel 350, e.g., the polymeric material could be permeable to water and oxygen and the electrochemical battery could be exposed to an aqueous fluid by diffusion through the polymeric material (i.e., the polymeric material forms a protective layer of the electrochemical battery).

The eye- and/or body-mountable devices as shown herein (e.g., 100, 300) could include one or more sensors (not shown) configured to detect physiological parameters of a body (e.g., concentrations of analytes in blood, sweat, tears, or other bodily fluids, an amount of blood in a portion of subsurface vasculature, an oxygenation state of blood, whether an eyelid is closed), properties of the environment of the device (e.g., an ambient illumination, a barometric pressure, a temperature), properties of the device (e.g., an acceleration, an orientation), or to detect some other information. Such sensors could include accelerometers, electrodes (e.g., electrodes of an electrochemical analyte sensors, electrodes of an electrophysiological sensor configured to detect a galvanic skin potential, an electrocardiogram, an electrooculogram, an electromyogram, or some other bioelectrical signal), light detectors, thermometers, gyroscopes, capacitance sensors, pressure sensors, strain gauges, light emitters, microphones, or other elements configured to detect one or more physical variables related to a property of interest. The eye- and/or body-mountable devices as shown here could operate such elements to measure physiological parameters or other information of interest at one or more points in time using power provided by an electrochemical battery and/or power provided by some other source (e.g., RF power provided by an external system via an antenna of a body-mountable device). Such measured properties and/or parameters could be recorded (e.g., in a memory of the device, for example, for later transmission to an external system), transmitted to an external system, indicated using elements of the device (e.g., using a display, using one or more light-emitting elements), used to determine a health state of a user, or used according to some other application.

Although devices including electrochemical batteries are described herein by way of example as eye- and body-mountable devices (e.g., an ophthalmic device), it is to be understood that the disclosed electrochemical battery can be applied in other contexts as well. For example, electrochemical batteries as disclosed herein may be included in implantable devices. In some contexts, an electrochemical battery and electronics powered thereby when the electrochemical battery is exposed to an aqueous fluid are situated to be substantially encapsulated by a bio-compatible polymeric material suitable for being in contact with an external body surface and/or for being implanted. In one example, a mouth-mountable device includes an electrochemical battery and electronics powered thereby and is configured to be mounted within an oral environment, such as adjacent a tooth or adhered to an inner mouth surface. In another example, an implantable medical device that includes an electrochemical battery and related electronics may be encapsulated in biocompatible material and implanted within a host organism.

In other examples, electrochemical batteries disclosed herein may be included in electronic devices that are not used in combination with a human body. For example, electrochemical batteries and related electronics disclosed herein may be included in body-mountable and/or implantable devices used in combination with an animal body. In another example, electrochemical batteries disclosed herein may be included in devices configured to operate in some other environment that includes an aqueous fluid to which an electrochemical battery could be exposed, such as a fluid or other element(s) of a river, lake, marsh, forest, prairie, reservoir, water supply, sanitary sewer system, or storm sewer system. For example, electrochemical batteries disclosed herein could be included in a low-power environmental sensor that is part of a distributed sensor network. Other applications for electrochemical batteries and related electronics as described herein are anticipated.

III. EXAMPLE ELECTRONICS OF A BODY-MOUNTABLE DEVICE

Figure 4:
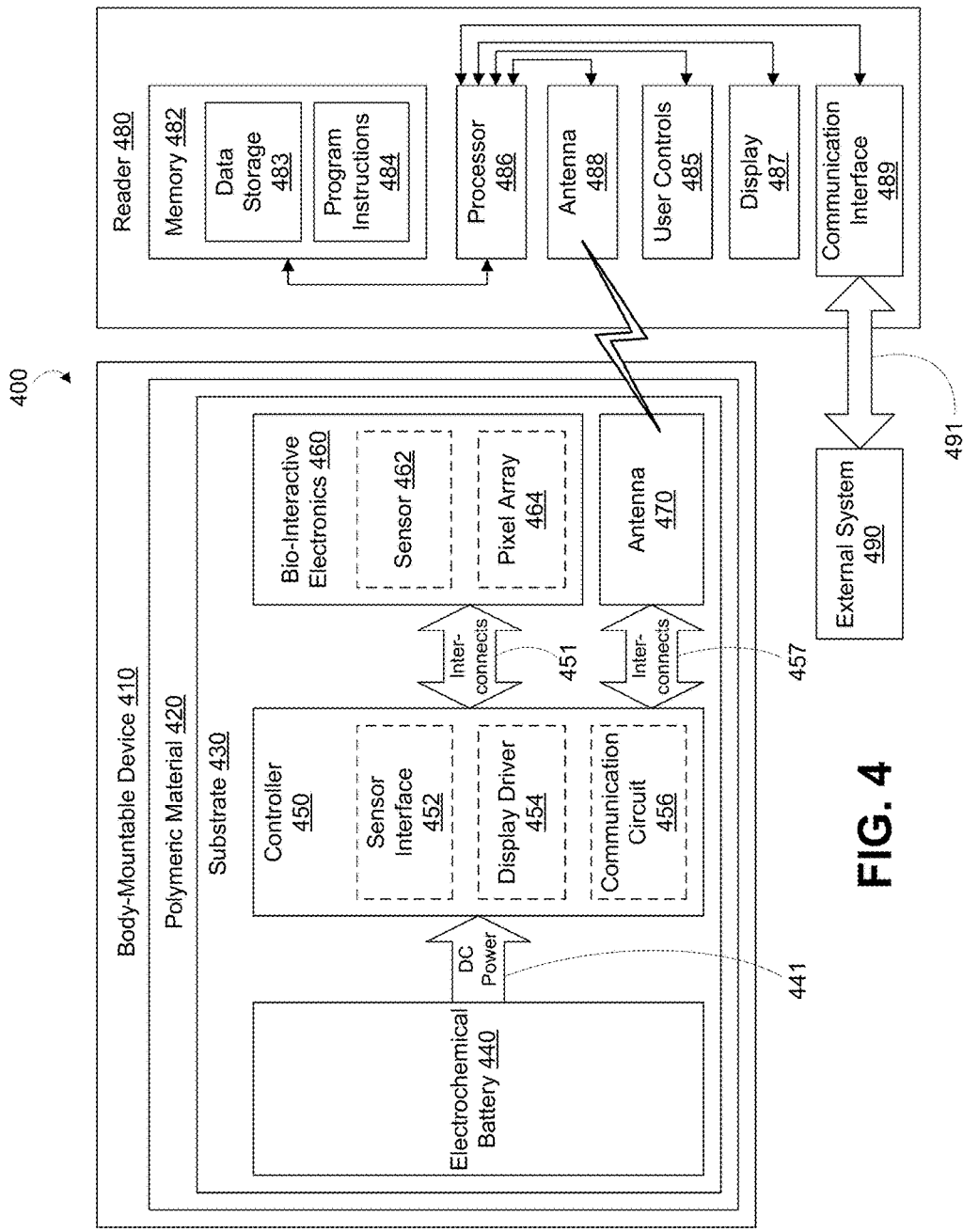
FIG. 4 is a block diagram of an example system that includes a body-mountable device in wireless communication with an external reader.

FIG. 4 is a block diagram of a system 400 that includes a body-mountable device 410 in wireless communication with an external reader 480. Exposed regions of the body-mountable device 410 are made of a polymeric material 420 formed to be contact-mounted to a body surface, e.g. to a corneal surface of an eye. A substrate 430 is embedded in the polymeric material 420 to provide a mounting surface for an electrochemical battery 440, a controller 450, bio-interactive electronics 460, and a communication antenna 470. The bio-interactive electronics 460 are operated by the controller 450. The electrochemical battery 440 supplies operating voltages to the controller 450 and/or the bio-interactive electronics 460 when an anode and a cathode of the electrochemical battery 440 are exposed to an aqueous fluid (e.g., tear fluid of an eye to which the body-mountable device 410 is mounted). The antenna 470 is operated by the controller 450 to communicate information to and/or from the body-mountable device 410. The antenna 470, the controller 450, the electrochemical battery 440, and the bio-interactive electronics 460 can all be situated on the embedded substrate 430. In examples wherein the body-mountable device 410 includes electronics and is configured to be contact-mounted to an eye, it is also referred to herein as an ophthalmic electronics platform.

To facilitate contact-mounting to an eye, the polymeric material 420 can have a concave surface configured to adhere ("mount") to a moistened corneal surface (e.g., by capillary forces with a tear film coating the corneal surface). Additionally or alternatively, the eye-mountable device 410 can be adhered by a vacuum force between the corneal surface and the polymeric material due to the concave curvature. While mounted with the concave surface against the eye, the outward-facing surface of the polymeric material 420 can have a convex curvature that is formed to not interfere with eye-lid motion while the eye-mountable device 410 is mounted to the eye. For example, the polymeric material 420 can be a substantially transparent curved polymeric disk shaped similarly to a contact lens.

Alternatively, the polymeric material 420, substrate 430, and/or other elements of the body-mountable device 410 can be formed to be mounted to and/or disposed within other environments. For example, the body-mountable device 410 could be configured to be mounted to a skin surface such that the electrochemical battery could be exposed to sweat to power the body-mountable device 410 to perform some functions (e.g., detecting one or more physiological properties of the skin to which the device is mounted). In another example, the body-mountable device 410 could be configured to mount to a skin surface and to include an elongate probe that is configure to penetrate skin such that a sensor, electrochemical battery, and/or other elements can be exposed to interstitial fluid or blood within the skin. Further, in some examples a device could include a substrate and an electrochemical battery disposed thereon (e.g., a cathode and a zinc-metal including anode) but could omit the polymeric material (e.g., the substrate could be configured to mount directly to a skin surface or other environment of interest).

The polymeric material 420 can include one or more biocompatible materials, such as those employed for use in contact lenses or other ophthalmic applications involving direct contact with the corneal surface. The polymeric material 420 can optionally be formed in part from such biocompatible materials or can include an outer coating with such biocompatible materials. The polymeric material 420 can include materials configured to moisturize the corneal surface, such as hydrogels and the like. In some instances, the polymeric material 420 can be a deformable ("non-rigid") material to enhance wearer comfort. In some instances, the polymeric material 420 can be shaped to provide a predetermined, vision-correcting optical power, such as can be provided by a contact lens.

The substrate 430 includes one or more surfaces suitable for mounting the bio-interactive electronics 460, the controller 450, the electrochemical battery 440, and the antenna 470. The substrate 430 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create anodes, cathodes, electrodes, interconnects, antennae, etc. In some embodiments, substantially transparent conductive materials (e.g., indium tin oxide) can be patterned on the substrate 430 to form circuitry, electrodes, etc. For example, the antenna 470 can be formed by depositing a pattern of gold or another conductive material on the substrate 430. Similarly, interconnects 451, 457 between the controller 450 and the bio-interactive electronics 460, and between the controller 450 and the antenna 470, respectively, can be formed by depositing suitable patterns of conductive materials on the substrate 430. A combination of microfabrication techniques including, without limitation, the use of photoresists, masks, deposition techniques and/or plating techniques can be employed to pattern materials on the substrate 430. The substrate 430 can be a relatively rigid material, such as polyethylene terephthalate ("PET"), parylene, or another material sufficient to structurally support the circuitry and/or electronics within the polymeric material 420. The body-mountable device 410 can alternatively be arranged with a group of unconnected substrates rather than a single substrate. For example, the controller 450 and a bio-sensor or other bio-interactive electronic component can be mounted to one substrate, while the antenna 470 is mounted to another substrate and the two can be electrically connected via the interconnects 457.

In some embodiments wherein the body-mountable device 410 is an eye-mountable device, the bio-interactive electronics 460 (and the substrate 430) can be positioned away from the center of the body-mountable device 410 and thereby avoid interference with light transmission to the eye through the center of the body-mountable device 410. For example, where the body-mountable device 410 is shaped as a concave-curved disk, the substrate 430 can be embedded around the periphery (e.g., near the outer circumference) of the disk. In some embodiments, the bio-interactive electronics 460 (and the substrate 430) can be positioned in the center region of the body-mountable device 410. The bio-interactive electronics 460 and/or substrate 430 can be substantially transparent to incoming visible light to mitigate interference with light transmission to the eye. Moreover, in some embodiments, the bio-interactive electronics 460 can include a pixel array 464 that emits and/or transmits light to be perceived by the eye according to display instructions. Thus, the bio-interactive electronics 460 can optionally be positioned in the center of the body-mountable device so as to generate perceivable visual cues to a wearer of the body-mountable device 410, such as by displaying information via the pixel array 464.

The substrate 430 can be shaped as a flattened ring with a radial width dimension sufficient to provide a mounting platform for the embedded electronics components. The substrate 430 can have a thickness sufficiently small to allow the substrate 430 to be embedded in the polymeric material 420 without influencing the profile of the body-mountable device 410, e.g., without influencing a profile of the body-mountable device 410 that is specified to allow the body-mountable device 410 to be contact-mounted to a cornea without causing discomfort to a wearer. The substrate 430 can have a thickness sufficiently large to provide structural stability suitable for supporting the electronics mounted thereon. For example, the substrate 430 can be shaped as a ring with a diameter of about 10 millimeters, a radial width of about 1 millimeter (e.g., an outer radius 1 millimeter larger than an inner radius), and a thickness of about 50 micrometers. The substrate 430 can optionally be aligned with the curvature of an eye-mounting surface of a body-mountable device 410 that is configured to mount to an eye (e.g., convex surface). For example, the substrate 430 can be shaped along the surface of an imaginary cone between two circular segments that define an inner radius and an outer radius. In such an example, the surface of the substrate 430 along the surface of the imaginary cone defines an inclined surface that is approximately aligned with the curvature of the eye mounting surface at that radius.

The electrochemical battery 440 includes an anode and a cathode as described elsewhere herein and is configured to provide an electrochemical potential between the anode and the cathode to power the body-mountable device 410 (e.g., to power the controller 450 and bio-interactive electronics 460) when the electrochemical battery is exposed to an aqueous fluid. The body-mountable device 410 could include a voltage regulator, boost converter, buck converter, a charge pump, or some other elements configured to use power provided by the electrochemical battery 440 to generate a specified voltage to power elements of the body-mountable device 410 (e.g., to power the controller 450). These elements could be formed on a chip with the controller 450 or could form separate components disposed on the substrate 430 and connected to the controller 430, electrochemical battery 440, and/or other components by interconnects. Additionally or alternatively, the controller 430 and/or other components could be configured to be powered directly by the electrochemical potential provided by the electrochemical battery 440.

The body-mountable device 410 could additionally be configured to harvest energy to power the controller 450. For example, a radio-frequency energy-harvesting antenna (e.g., antenna 470 or some other antenna (not shown) can capture energy from incident radio radiation. A rectifier/regulator can be used to condition the captured energy to a stable DC supply voltage that is supplied to the controller 450. For example, the antenna 470 could receive incident radio frequency radiation. Varying electrical signals on the leads of the antenna 470 are output to the rectifier/regulator. The rectifier/regulator rectifies the varying electrical signals to a DC voltage and regulates the rectified DC voltage to a level suitable for operating the controller 450. The rectifier/regulator can include one or more energy storage devices to mitigate high frequency variations in the ambient energy gathered by the antenna 470. For example, one or more energy storage devices (e.g., a capacitor, an inductor, etc.) can be connected in parallel across the outputs of the rectifier to regulate the DC supply voltage and configured to function as a low-pass filter. RF energy received in this manner could be used to augment the power received from the electrochemical battery 440, e.g., to perform operations that require more power than is provided by the electrochemical battery 440 (e.g., to transmit information, to perform calculations to convert measured sensor data into physiological parameter data, to operate a display to provide an indication related to a sensor measurement).

The controller 450 is turned on when the DC supply voltage 441 is provided to the controller 450 (e.g., by mounting the body-mountable device 410 to an eye such that the electrochemical battery 440 is exposed to a tear film of the eye), and the logic in the controller 450 operates the bio-interactive electronics 460 and the antenna 470. The controller 450 can include logic circuitry configured to operate the bio-interactive electronics 460 so as to interact with a biological environment of the body-mountable device 410. The interaction could involve the use of one or more components, such as electrodes, light emitters, light detectors, thermometers, accelerometers, or other elements of the sensor 462, in bio-interactive electronics 460 to obtain input from the biological environment (e.g., from a tear fluid or other fluid from the biological environment). Additionally or alternatively, the interaction could involve the use of one or more components, such as pixel array 464, to provide an output to the biological environment.

In one example, the controller 450 includes a sensor interface module 452 that is configured to operate the sensor 462. The sensor 462 can be operated to generate an output related to a physiological parameter (e.g., a concentration of an analyte, an amount and/or color of blood in a portion of subsurface vasculature, an electrical potential between two or more points of tissue) of the biological environment. For example, the sensor interface 452 could include an electrode voltage source configured to apply a specified voltage between a working electrode and a reference electrode of the sensor 462 such that a current through the working electrode of the sensor 462 is related to a concentration of an analyte (e.g., glucose) in the biological environment. The sensor interface 452 could include voltage sources, current sources, digital-to-analog converters, analog-to-digital converters, amplifiers, comparators, oscillators, or other electronic components configured to operate a sensor 462 to measure some physiological parameter of a biological environment of the body-mountable device 410. Additionally or alternatively, one or more electronic elements or systems configured to operate the sensor 462 could be disposed as part of the bio-interactive electronics 460 (e.g., by being formed from the same integrated circuit or semiconductor wafer as a photodiode or other element(s) of the sensor 462) or as part of some other aspect of the body-mountable device 410.

The controller 450 can optionally include a display driver module 454 for operating a pixel array 464. The pixel array 464 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 454. Such a pixel array 464 can also optionally include more than one color of pixels (e.g., red, green, and blue pixels) to render visual content in color. The display driver module 454 can include, for example, one or more data lines providing programming information to the separately programmed pixels in the pixel array 464 and one or more addressing lines for setting groups of pixels to receive such programming information. Such a pixel array 464 situated on an eye can also include one or more lenses to direct light from the pixel array to a focal plane perceivable by the eye.

The controller 450 can also include a communication circuit 456 for sending and/or receiving information via the antenna 470. The communication circuit 456 can optionally include one or more oscillators, mixers, frequency injectors, etc. to modulate and/or demodulate information on a carrier frequency to be transmitted and/or received by the antenna 470. In some examples, the body-mountable device 410 is configured to indicate an output from a bio-sensor by modulating an impedance of the antenna 470 in a manner that is perceivably by the external reader 480. For example, the communication circuit 456 can cause variations in the amplitude, phase, and/or frequency of backscatter radiation from the antenna 470, and such variations can be detected by the reader 480.

The controller 450 is connected to the bio-interactive electronics 460 via interconnects 451. For example, where the controller 450 includes logic elements implemented in an integrated circuit to form the sensor interface module 452 and/or display driver module 454, a patterned conductive material (e.g., gold, platinum, palladium, titanium, copper, aluminum, silver, metals, combinations of these, etc.) can connect a terminal on the chip to the bio-interactive electronics 460. Similarly, the controller 450 is connected to the antenna 470 via interconnects 457.

It is noted that the block diagram shown in FIG. 4 is described in connection with functional modules for convenience in description. However, embodiments of the body-mountable device 410 can be arranged with one or more of the functional modules ("sub-systems") implemented in a single chip, integrated circuit, and/or physical feature. That is, the functional blocks in FIG. 4 shown as the bio-interactive electronics block 460 and controller block 450 need not be implemented as separated modules. Moreover, one or more of the functional modules described in FIG. 4 can be implemented by separately packaged chips electrically connected to one another.

The external reader 480 includes an antenna 488 (or group of more than one antenna) to send and receive wireless signals 471 to and from the body-mountable device 410. The external reader 480 also includes a computing system with a processor 486 in communication with a memory 482. The external reader 480 can also include one or more of user controls 485, a display 487, and a communication interface 489. The memory 482 is a non-transitory computer-readable medium that can include, without limitation, magnetic disks, optical disks, organic memory, and/or any other volatile (e.g. RAM) or non-volatile (e.g. ROM) storage system readable by the processor 486. The memory 482 can include a data storage 483 to store indications of data, such as sensor readings (e.g., related to the sensor 462), program settings (e.g., to adjust behavior of the body-mountable device 410 and/or external reader 480), etc. The memory 482 can also include program instructions 484 for execution by the processor 486 to cause the external reader 480 to perform processes specified by the instructions 484. For example, the program instructions 484 can cause external reader 480 to perform any of the function described herein. For example, program instructions 484 may cause the external reader 480 to provide a user interface that allows for retrieving information communicated from the body-mountable device 410 (e.g., sensor outputs or other information related to the sensor 462) by displaying that information on the display 487 in response to commands input through the user controls 485. The external reader 480 can also include one or more hardware components for operating the antenna 488 to send and receive the wireless signals 471 to and from the body-mountable device 410. For example, oscillators, frequency injectors, encoders, decoders, amplifiers, filters, etc. can drive the antenna 488 according to instructions from the processor 486.

The external reader 480 can also be configured include a communication interface 489 to communicate signals via a communication medium 491 to and from a remote system 490. For example, the remote system 490 may be a smart phone, tablet computer, laptop computer, or personal computer, and communication interface 489 and communication medium 491 may be a Bluetooth module and wireless Bluetooth communication signals, respectively. In this example, the external reader 480 may be configured to send ion concentration data collected by the biosensor 460 to the smart phone, tablet computer, laptop computer, or personal computer for storage and offline analysis. In another example, the remote system 490 is a server at a clinic or physician's office, the communication interface 489 is a WiFi radio module, and the communication medium 491 is elements of the internet sufficient to enable the transfer of data between the remote server and the WiFi radio module. A physician may use this data to make determinations or diagnoses related to the subject's condition. Further, the external reader 480 may be configured to receive signals from a remote server, such as instructions sent by a physician at a remote location to, for example, increase or decrease sampling frequency. Communication interface 489 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 480 can be a smart phone, digital assistant, or other portable computing device with wireless connectivity sufficient to provide the wireless communication link 471. The external reader 480 can also be implemented as an antenna module that can be plugged into a portable computing device, such as in an example where the communication link 471 operates at carrier frequencies not commonly employed in portable computing devices. In some instances, the external reader 480 is a special-purpose device configured to be worn relatively near a mounting location of the body-mountable device 410 on the wearer's body (e.g., near a wearer's eye) to allow the wireless communication link 471 to operate with a low power budget. For example, the external reader 480 can be integrated in a piece of jewelry such as a necklace, earring, etc. or integrated in an article of clothing worn near the head, such as a hat, headband, etc. The external reader 480 could also be implemented in eye glasses or a head-mounted display.

In order for the body-mountable device 410 perform certain functions (e.g., to compute values of a physiological parameter based on measurements of the sensor 462, to operate a sensor that requires more power than the electrochemical battery 440 can supply, to transmit information related to measurements made by the sensor 462), the external reader 480 can emit radio frequency radiation 471 that is harvested to power the eye-mountable device 410. Radio frequency electrical signals captured by an energy harvesting antenna (and/or the communication antenna 470) are rectified and/or regulated and a regulated DC supply voltage is provided to the controller 450. The radio frequency radiation 471 thus powers the electronic components within the body-mountable device 410. This power can be provided in combination with or alternative to power provided by the electrochemical battery 440. Once powered in this way, the controller 450 can perform functions, e.g., can operate a sensor (e.g., 462) to measure a physiological property, the pixel array 464 to provide an indication (e.g., an indication related to one or more measurements made by the sensor 462), the antenna 470 to transmit information, or other functions.

The controller 450 can operate the antenna 470 to communicate information (e.g., sensor readings) to the external reader 480 (e.g., via the communication circuit 456). Additionally or alternatively, the controller 450 can operate the antenna 470 to communicate other information. For example, the controller 450 could be configured to determine one or more properties of the biological environment based on one or more sensor readings (e.g., could determine an oxygen saturation of blood based on relative intensities of light received from the blood within respective ranges of wavelengths) and to subsequently communicate the determined one or more properties to the external reader 480 using the antenna 470. In another example, the digital output of an analog-to-digital convertor or other component(s) of the sensor interface 452 could be indicated or otherwise communicated to the external reader 480 using the antenna 470. Sensor readings or other information can be communicated by, for example, modulating an impedance of the communication antenna 470 such that the modulation in impedance is detected by the external reader 480. The modulation in antenna impedance can be detected by, for example, detecting backscatter radiation reflected by the antenna 470.

In some embodiments, the external reader 480 can operate to non-continuously ("intermittently") communicate with and/or supply energy to the body-mountable device 410. For example, radio frequency radiation 171 can be supplied to power the eye-mountable device 110 long enough to carry out a light measurement and communicate the results. For example, the electrochemical battery 440 can provide sufficient power to perform a plurality of measurements over an extended period using the sensor 462 and to record the measurements (e.g., in a memory of the controller 450). In such an example, radio frequency radiation 471 supplied by the external reader 480 can be considered an interrogation signal from the external reader 480 to the body-mountable device 410 to request a transmission of information. By periodically interrogating the body-mountable device 410 (e.g., by supplying radio frequency radiation 471 to provide additional power to the device) and storing the recorded sensor results responsively transmitted from the body-mountable device 410 (e.g., via the data storage 483), the external reader 480 can accumulate a set of sensor measurements and/or related determined physiological parameters (e.g., analyte concentrations, blood volumes, blood oxygen saturations, pulse rates) over time without continuously interacting with the body-mountable device 410.

IV. EXAMPLE METHODS

Figure 5:
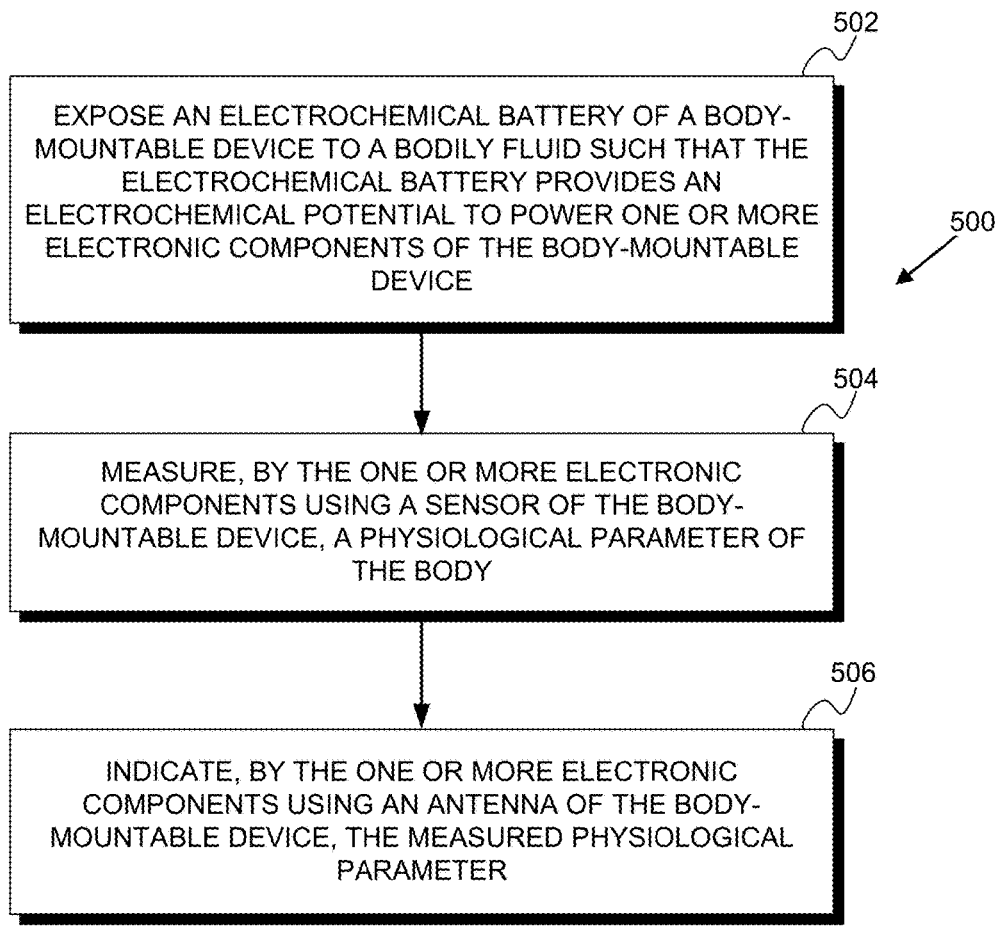
FIG. 5 is a flowchart of an example process.

FIG. 5 is a flowchart of a method 500 for operating a body-mountable device to measure a physiological parameter (e.g., a concentration of an analyte in a fluid, a flow rate of blood, a pulse rate, a bioelectrical potential or signal, a blood oxygenation) using power provided by an electrochemical battery of the body-mountable device. The body-mountable device includes (i) a shaped polymeric material (e.g., a hydrogel shaped to form an ophthalmic lens), (ii) a substrate at least partially embedded within the shaped polymeric material (e.g., embedded within the polymeric material such that one or more of an electrochemical battery, an electrochemical sensor, an electrophysiological electrode, or some other element(s) are exposed to the environment of the device), (iii) an antenna disposed on the substrate, (iv) a sensor disposed on the substrate, (v) an electrochemical battery disposed on the substrate, and (vi) one or more electronic components (e.g., a controller) electrically connected to the antenna, the sensor, and the electrochemical battery. The electrochemical battery includes a cathode and an anode that includes a layer of zinc metal. The electrochemical battery is configured to provide an electrochemical potential to power the one or more electronics when the body-mountable device is exposed to a bodily fluid (e.g., when water and oxygen from the bodily fluid come into contact with the anode and cathode of the electrochemical battery).

The method 500 includes exposing the electrochemical battery to a bodily fluid such that the electrochemical battery provides an electrochemical potential to power the one or more electronic components (502). In some examples, the body-mountable device could be formed to substantially conform to a cornea of an eye of the body, and exposing the battery to a bodily fluid (502) could include mounting the device on the cornea such that the electrochemical battery is exposed at least intermittently to a tear fluid of the eye. Alternatively, the body-mountable device could be formed to mount to skin, to mucosa within the mouth, or to the surface of some other external or internal tissue of a body and exposing the battery to a bodily fluid (502) could include mounting the device to the skin, mucosa, or other tissue such that the electrochemical battery is exposed at least intermittently to sweat, saliva, interstitial fluid, mucus, blood, cerebrospinal fluid, tears, lymph, chyme, bile, or some other aqueous fluid of a body.

The method 500 includes measuring, by the one or more electronic components using the sensor, a physiological parameter of the body (504). This could include applying a voltage (i.e., applying power) to electrodes of the sensor, e.g., to amperometrically detect a concentration of an analyte in a bodily fluid to which the sensor is exposed. The one or more electronic components using the sensor could include setting one or more parameters or controls of the electronics (e.g., setting reference voltages, clock frequencies, current sink values) such that an electronic signal (e.g., a voltage or current output of one or more electrodes, a current through a photodiode) of the sensor is related to the physiological parameter to be measured. Such an electronic signal could be digitized (e.g., using an analog-to-digital converter), used to set a frequency of an oscillator (e.g., an oscillator configured to drive an antenna), or used in some other way by the one or more electronics, e.g., to record information related to the measure physiological property, to indicate (e.g., transmit) information related to the measure physiological property, or according to some other application.

The method 500 further includes indicating, by the one or more electronic components using the antenna, the measured physiological parameter (506). In some examples, this could include recording information related to the measured parameter (e.g., recording a digital code output from an analog-to-digital converter, recording a value of the physiological parameter that is determined based on a measurement generated by the sensor) and subsequently using such recorded information (e.g., transmitting the recorded information, determining a health state based on the recorded information, providing an indication related to the recorded information to a user of the device). Additionally or alternatively, the body-mountable device could provide an indication (e.g., using an antenna of the body-mountable device, using a user interface of the device) related to the measured physiological process, and some other system (e.g., a reader configured to wirelessly communicate with and/or power the body-mountable device) could receive the indication. The method 500 could include additional steps or elements in addition to those depicted in FIG. 5 (i.e., 502, 504, 506).

Figure 6:
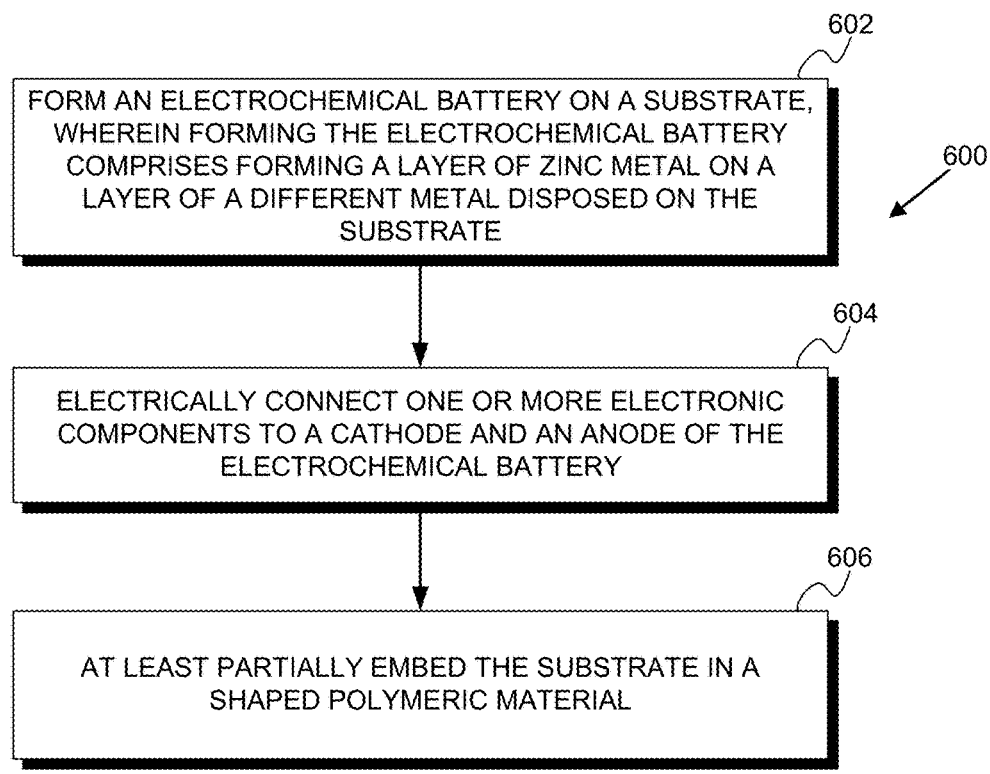
FIG. 6 is a flowchart of an example process.

FIG. 6 is a flowchart of a method 600 for fabricating a body-mountable device as described herein. The method 600 includes forming an electrochemical battery on a substrate, wherein forming the electrochemical battery comprises disposing a layer of zinc metal on a layer of a different metal (e.g., on a metal trace) disposed on the substrate (602). The formed electrochemical battery is configured to provide an electrochemical potential between an anode and a cathode of the electrochemical battery when exposed to a bodily fluid (e.g., blood, sweat, tears). The anode of the electrochemical battery includes the layer of zinc metal disposed on the layer of the different metal (e.g., the layer of gold, copper, silver, platinum, or some other metal). Forming an electrochemical battery on a substrate (602) could include forming the layer of the different metal and/or the cathode on the substrate by sputtering, photopatterning, laser ablation, or other means for depositing and patterning a metal layer (e.g., for forming metal traces composed of copper, gold, aluminum, steel, silver, platinum, or other metals of combinations of metals) according to a specified geometry on a substrate. The formed cathode could include a metal configured to catalyze the production of hydroxide ions to oxidize zinc metal at the anode and to provide a means for the cathode to emit negative charge into an aqueous fluid (e.g., into water that has diffused through a protective layer to the cathode and anode from a bodily fluid to which the electrochemical battery is exposed). For example, the cathode could include platinum (e.g., could be composed of platinum, could be a layer of a different metal (e.g., a metal trace) that has a surface layer or coating of platinum).

The layer of zinc metal could be disposed on the layer of the different metal by a variety of processes. In some examples, the layer of zinc metal could be deposited on the layer of the different metal by vacuum deposition (e.g., physical vapor deposition, chemical vapor deposition, sputtering). In other examples, an ink or other solution containing a zinc nano-powder suspended in a carrier fluid could be deposited on the layer of the different metal. The carrier fluid of the ink or other solution could then be evaporated or otherwise removed, leaving a layer of zinc metal nanoparticles on the metal trace. In some examples, the layer of zinc metal could be formed on the layer of the different metal by electroplating. For example, the layer of the different metal could be exposed to (e.g., submerged in a container filled with) an electroplating solution and a voltage could be applied between the layer of the different metal and the electroplating solution (e.g., a voltage of approximately −2.5 volts applied via a carbon counter electrode disposed in the electroplating solution). An amount, thickness, or other properties of the layer of zinc metal disposed on the layer of the different metal could be controlled by controlling the magnitude of the applied voltage, applied current, and/or the time over which the voltage and/or current is applied. The electroplating solution could include a variety of zinc-containing compounds at a variety of concentrations. For example, the electroplating solution could include approximately 50 grams per liter of zinc chloride ($ZnCl_2$) and approximately 150 grams per liter of ammonium chloride ($NH_4Cl$). Other electroplating solutions are anticipated.

The method 600 includes electrically connecting one or more electronic components to the cathode and the anode of the electrochemical battery (604). This could include forming metal traces on the substrate (e.g., by sputtering, lithography, or other means) to form circuitry, antennas, electrodes, or other elements and subsequently disposing the electronics components on the formed metal traces (e.g., by a pick-and-place machine) and electrically connecting the electronic components (e.g., connecting pads of the components) to corresponding locations on the metal traces (e.g., by solder reflow, by applying an anisotropic conductive material, by applying a conductive adhesive, by wire-bonding, by some other means). The one or more electronic components could be any components configured to receive power from the formed electrochemical battery when the electrochemical battery is exposed to an aqueous fluid (e.g., a bodily fluid such as blood, sweat, tears, or interstitial fluid) and to use the received power to perform some functions. For example, the electronic components could include a controller configured to use the provided power to measure a physiological parameter (e.g., a concentration of an analyte in the aqueous fluid to which the electrochemical battery is exposed) and to indicate the measured parameter to a user, transmit the measured parameter to an external system, record the measured parameter in a memory, or to perform some other functions. The one or more electronic components could include electrodes, light emitter, light detectors, or other elements of a sensor. Additionally or alternatively, electrodes or other elements of a sensor could be formed from metal traces or other elements disposed on the substrate.

The method 600 includes at least partially embedding the substrate in a shaped polymeric material (606). This could include embedding the substrate within an ophthalmic lens (e.g., an ophthalmic lens composed of a hydrogel) and/or forming such an ophthalmic lens around the substrate. At least partially embedding the substrate in a shaped polymeric material (606) could include forming the shaped polymeric material such that the electrochemical battery, one or more sensors, or some other elements or portions of the substrate are exposed to an environment of the shaped polymeric material, e.g., such that the electrochemical battery, one or more sensors, or some other elements could be exposed to an aqueous bodily fluid when the shaped polymeric material is mounted to or otherwise disposed proximate a biological tissue (e.g., mounted to a corneal surface of an eye). This could include forming one or more channels in the shaped polymeric material, e.g., by ablating or removing portions of a formed polymeric material and/or forming the shaped polymeric material in a mold that contains the substrate and elements disposed thereon and that includes protrusions corresponding to one or more channels to be formed in the shaped polymeric material.

The method 600 could include additional steps or elements in addition to those depicted in FIG. 6 (i.e., 602, 604, 606). For example, the method 600 could include forming a water- and oxygen-permeable protective layer (e.g., a layer formed of a hydrogel) over the anode and cathode of the electrochemical battery.

V. EXPERIMENTAL RESULTS

Figure 7:
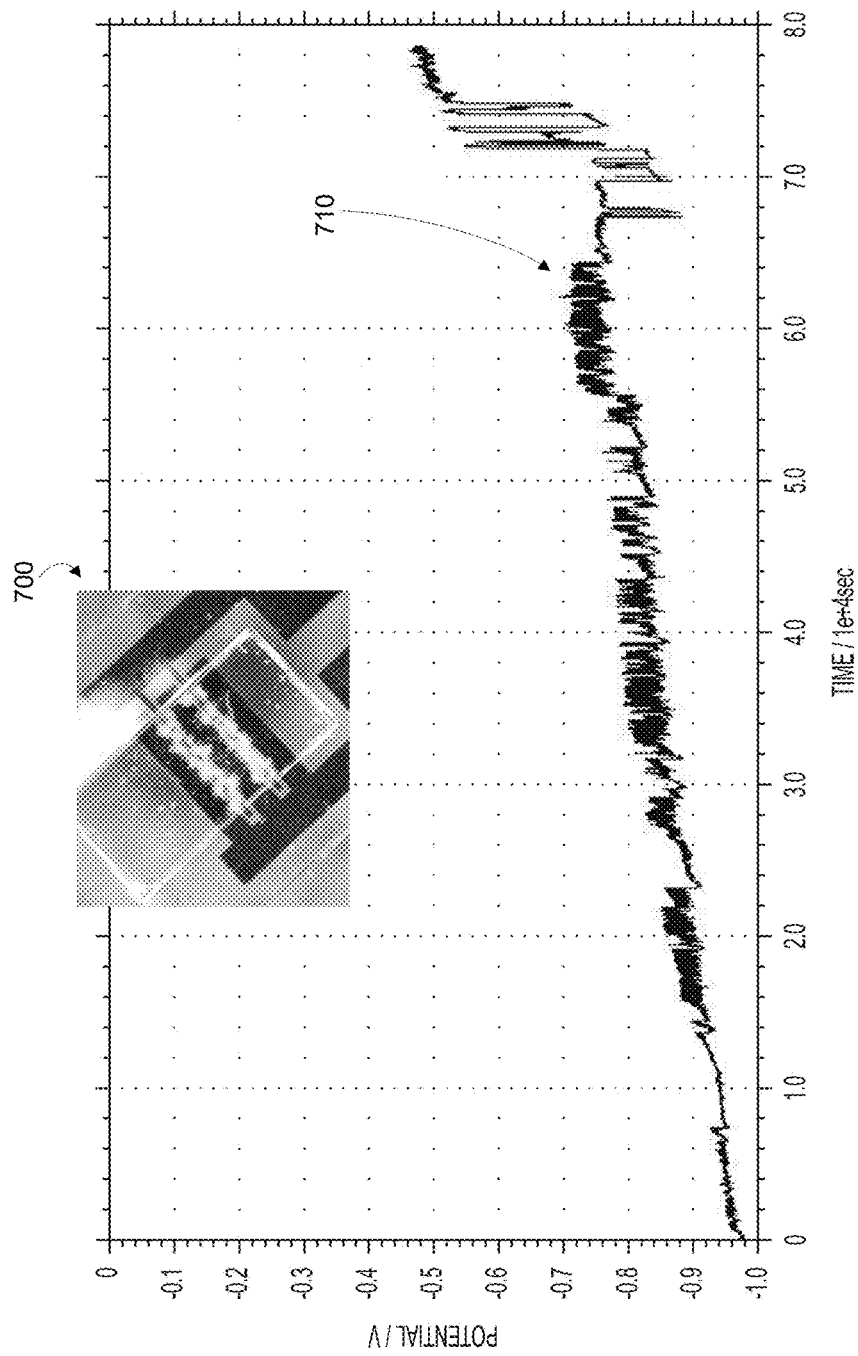
FIG. 7 is a plot of the voltage output by an example battery over time when a load is applied to the battery.

FIG. 7 illustrates an example battery 700 as described herein. The example battery 700 includes two platinum anodes on which zinc has been electroplated. The two anodes are 50 microns wide by 1 millimeter long. The zinc was electroplated on the platinum of the anodes by exposing the platinum anodes to a solution containing 50 g/L $ZnCl_2$ and 150 g/L $NH_4Cl$ and applying a controlled potential of −2.5 V to the platinum anodes, relative to an external carbon counter electrode. This controlled potential was applied until a 20 micron thick layer of zinc was deposited on the anodes, resulting in approximately 14 micrograms of zinc metal having been deposited on the anodes. The example battery also includes three platinum cathodes, between which the anodes are disposed. The cathodes are 250 microns wide and 1 millimeter long. As shown in FIG. 7, the battery 700 has been partially discharged in a phosphate buffered saline solution, and an insoluble white $Zn(OH)_2$ precipitate has formed along the anodes.

FIG. 7 also illustrates an experimentally measured voltage discharge curve 710. The voltage discharge curve 710 indicates the voltage generated by the battery 700 over time when the battery 700 is exposed to a phosphate buffered saline solution and connected to a load such that the battery is discharged at a constant 200 nA current. Under these conditions, the battery exhibited an approximately 12 microamp-hour capacity. The battery 700 generated more than 0.7 volts for over seven hours under these conditions.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures. Further, note that while example embodiments of electrochemical batteries are described in connection with body-mountable devices, electrochemical batteries described herein could be incorporated into other devices or contexts, e.g., devices configured to provide electrical power when exposed to an aqueous fluid of an animal body (e.g., mounted to a skin surface, eye surface, mucosal surface, within a body cavity or tissue, or other location and exposed to blood, sweat, tears, cerebrospinal fluid, interstitial fluid, or other aqueous fluids), a natural environment (e.g., a lake, stream, river, marsh, or other environment wherein the electrochemical battery could be exposed to an aqueous fluid), an artificial environment (e.g., aqueous fluids of a water treatment process, a pharmaceutical synthesis process, a reservoir, a food processing process, a composting process, a sewage system, a municipal water supply system), or some other environment. Such electrochemical batteries could provide power for electronics or other elements configured to provide some functions, e.g., to measure and log and/or transmit some property of the environment of devices including the electrochemical batteries, e.g., the concentration of an analyte of interest in fluid of a natural environment, water treatment process, pharmaceutical synthesis process, or some other environment.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
   a shaped polymeric material;
   a substrate at least partially embedded within the shaped polymeric material;
   an electrochemical battery disposed on the substrate and comprising:
      a cathode; and
      an anode, wherein the anode comprises zinc metal, wherein the electrochemical battery provides an electrochemical potential between the anode and the cathode when the anode and cathode are exposed to an aqueous fluid from an environment of the body-mountable device, and wherein the anode and the cathode comprise interdigitated electrodes; and
   one or more electronic components electrically connected to the cathode and the anode, wherein the one or more electronic components are configured to receive power from the electrochemical battery when the electrochemical battery is exposed to the aqueous fluid.

2. The body-mountable device of claim 1, wherein the aqueous fluid is a tear fluid of an eye, wherein the shaped polymeric material has a concave surface and a convex surface, wherein the concave surface is configured to be removably mounted over a corneal surface of the eye and the convex surface is configured to be compatible with eyelid motion when the concave surface is so mounted.

3. The body-mountable device of claim 1, further comprising:
   an antenna disposed on the substrate, wherein the one or more electronic components are disposed on the substrate and electrically connected to the antenna; and
   a sensor disposed on the substrate, wherein the one or more electronic components are electrically connected to the antenna, wherein the one or more electronic components are configured to: (i) operate the sensor to measure a physiological parameter of a body when the body-mountable device is mounted to the body and in contact with an aqueous fluid of the body; and (ii) use the antenna to indicate the measured physiological parameter.

4. The body-mountable device of claim 1, wherein the electrochemical battery further comprises a protective layer, wherein the protective layer is permeable to water and to oxygen.

5. The body-mountable device of claim 4, wherein the protective layer comprises a hydrogel that comprises units of hydroxyethyl methacrylate.

6. The body-mountable device of claim 4, wherein the shaped polymeric material comprises the protective layer.

7. The body-mountable device of claim 1, wherein the cathode comprises platinum.

8. The body-mountable device of claim 1, wherein the anode comprises a layer of zinc metal disposed on a layer of a different metal that is disposed on the substrate.

9. A method comprising:
   operating a body-mountable device at a body location where a bodily fluid is at least intermittently present, wherein the body-mountable device comprises:
      a shaped polymeric material;
      a substrate at least partially embedded within the shaped polymeric material;
      an electrochemical battery disposed on the substrate and comprising:
         a cathode; and
         an anode, wherein the anode comprises zinc metal, wherein the electrochemical battery provides an electrochemical potential between the anode and the cathode when the anode and cathode are exposed to the bodily fluid, and wherein the anode and the cathode comprise interdigitated electrodes; and
      one or more electronic components electrically connected to the cathode and the anode, wherein the operating comprises:
   exposing the electrochemical battery to the bodily fluid such that the electrochemical battery provides an electrochemical potential between the anode and the cathode to power the one or more electronic components.

10. The method of claim 9, wherein the bodily fluid is a tear fluid of an eye, wherein the shaped polymeric material has a concave surface and a convex surface, wherein the concave surface is configured to be removably mounted over a corneal surface of the eye and the convex surface is configured to be compatible with eyelid motion when the concave surface is so mounted.

11. The method of claim 9, wherein the electrochemical battery further comprises a protective layer, wherein the protective layer is permeable to water and to oxygen.

12. The method of claim 11, wherein the protective layer comprises a hydrogel that comprises units of hydroxyethyl methacrylate.

13. The method of claim 11, wherein the shaped polymeric material comprises the protective layer.

14. The method of claim 9, wherein the body-mountable device further comprises:
   an antenna disposed on the substrate, wherein the one or more electronic components are disposed on the substrate and electrically connected to the antenna; and
   a sensor disposed on the substrate, wherein the one or more electronic components are electrically connected to the antenna, wherein the operating further comprises:
   measuring, by the one or more electronic components using the sensor, a physiological parameter of the body; and
   indicating, by the one or more electronic components using the antenna, the measured physiological parameter.

15. The method of claim 9, wherein the cathode comprises platinum.

16. The method of claim 9, wherein the anode comprises a metal trace disposed on the substrate.

* * * * *